United States Patent
Zhu et al.

(10) Patent No.: US 8,738,155 B2
(45) Date of Patent: *May 27, 2014

(54) SYSTEM FOR DETERMINING RELATIVE POSITION BETWEEN NEUROSTIMULATION LEADS

(71) Applicant: Boston Scientific Neuromodulation Corporation, Irvine, CA (US)

(72) Inventors: Changfang Zhu, Valencia, CA (US); Michael Moffitt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/903,713

(22) Filed: May 28, 2013

(65) Prior Publication Data
US 2013/0261718 A1    Oct. 3, 2013

Related U.S. Application Data

(63) Continuation of application No. 13/536,688, filed on Jun. 28, 2012, now Pat. No. 8,463,402, and a continuation of application No. 12/550,136, filed on Aug. 28, 2009, now Pat. No. 8,233,992.

(51) Int. Cl.
*A61N 1/00* (2006.01)
(52) U.S. Cl.
USPC .......................................... 607/117
(58) Field of Classification Search
USPC .......................................... 607/117
See application file for complete search history.

(56) References Cited

U.S. PATENT DOCUMENTS

| | | | |
|---|---|---|---|
| 6,516,227 | B1 | 2/2003 | Meadows et al. |
| 6,895,280 | B2 | 5/2005 | Meadows et al. |
| 6,993,384 | B2 | 1/2006 | Bradley et al. |
| 7,317,948 | B1 | 1/2008 | King et al. |
| 7,831,307 | B1 * | 11/2010 | Moffitt ............................ 607/46 |
| 2003/0139781 | A1 | 7/2003 | Bradley et al. |
| 2007/0168004 | A1 | 7/2007 | Walter |

(Continued)

FOREIGN PATENT DOCUMENTS

| WO | WO 2006/107848 A2 | 10/2006 |
|---|---|---|
| WO | WO 2007/097873 A1 | 8/2007 |

OTHER PUBLICATIONS

Cameron, Tracy, Safety and efficacy of spinal cord stimulation for the treatment of chronic pain: a 20-year literature review, J. Neurosurg (Spine 3) 100:254-267, 2004.

(Continued)

*Primary Examiner* — George Manuel
(74) *Attorney, Agent, or Firm* — Vista IP Law Group LLP

(57) ABSTRACT

A method and neurostimulation control system for operating two leads disposed adjacent tissue of a patient are provided. A plurality of cross-lead electrical parameters are measured to generate a measured electrical profile of the electrode leads. A plurality of cross-lead electrical parameters are estimated to generate a first reference electrical profile for the electrode leads in a first known staggered configuration. The first reference electrical profile is spatially shifted to generate a second reference electrical profile for the electrode leads in a second known staggered configuration. The measured electrical profile is compared to the first and second reference electrical profiles, and a longitudinal stagger between the electrode leads is quantified based on the comparison.

18 Claims, 9 Drawing Sheets

(56) References Cited

U.S. PATENT DOCUMENTS

| | | | |
|---|---|---|---|
| 2007/0168007 | A1 | 7/2007 | Kuzma et al. |
| 2008/0125833 | A1 | 5/2008 | Bradley et al. |
| 2009/0196472 | A1 | 8/2009 | Goetz et al. |
| 2010/0057177 | A1 | 3/2010 | Moffitt et al. |
| 2010/0137944 | A1 | 6/2010 | Zhu |

OTHER PUBLICATIONS

Holsheimer, Jan et al., Clinical Evaluation of Paresthesia Steering with a New System for Spinal Cord Stimulation, Neurosurgery, vol. 42, No. 3, Mar. 1998, 541-549.

Holsheimer, Jan et al., Optimum electrode geometry for spinal cord stimulation: the narrow bipole and tripole, Med. & Biol. Eng. & Comput., 1997, 35, 493-497.

Lee, Dongchul et al., Selective neural activation by field sculpting: Results from a new computer model for spinal cord stimulation, 16th Annual Computational Neuroscience Meeting, Jul. 7-12, 2007, Toronto, Canada: 177.

Struijk, J. J. et al., Transverse tripolar spinal cord stimulation: theoretical performance of a dual channel system, Med. & Biol. Eng. & Comput., 1996, 34, 273-279.

PCT International Preliminary Report on Patentability (Chapter I of the Patent Cooperation Treaty) for PCT/US2010/047031, Applicant: Boston Scientific Neuromodulation Corporation, Form PCT/IB/326 and 373, dated Mar. 8, 2012 (9pages).

PCT International Search Report for PCT/US2010/047031, Applicant: Boston Scientific Neuromodulation Corporation, Form PCT/ISA/210 and 220, dated Nov. 18, 2010 (6 pages).

PCT Written Opinion of the International Search Authority for PCT/US2010/047031, Applicant: Boston Scientific Neuromodulation Corporation, Form PCT/ISA/237, dated Nov. 18, 2010 (7 pages).

PCT Communication, Form PCT/ISA/224, dated Dec. 21, 2010 from related International Application No. PCT/US2010/047031 indicating that the previous International Search Report and Written Opinion issued on Nov. 18, 2010 contained error (1 page).

Corrected PCT International Search Report for PCT/US2010/047031, Applicant: Boston Scientific Neuromodulation Corporation, Form PCT/ISA/210 and 220, dated Dec. 21, 2010 (6 pages).

Corrected PCT Written Opinion of the International Search Authority for PCT/US2010/047031, Applicant: Boston Scientific Neuromodulation Corporation, Form PCT/ISA/237, dated Dec. 21, 2010 (7 pages).

\* cited by examiner

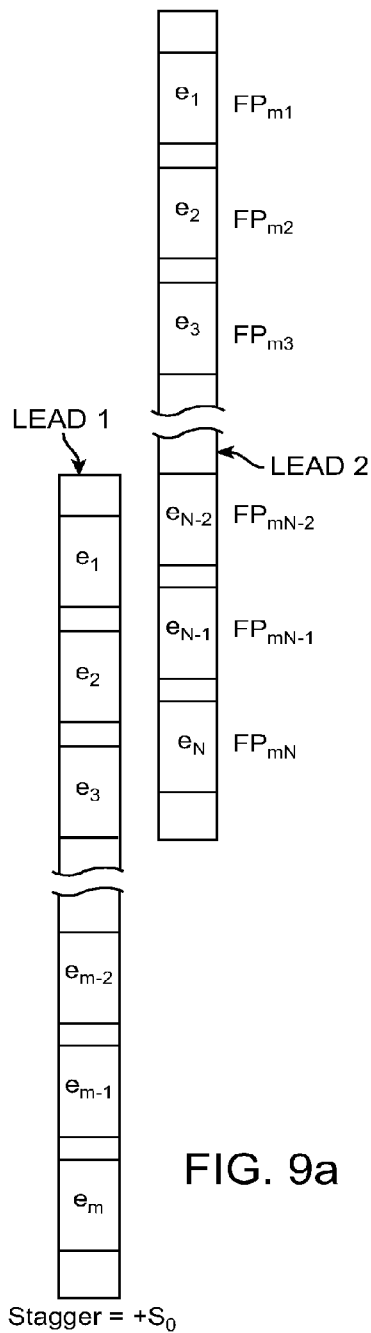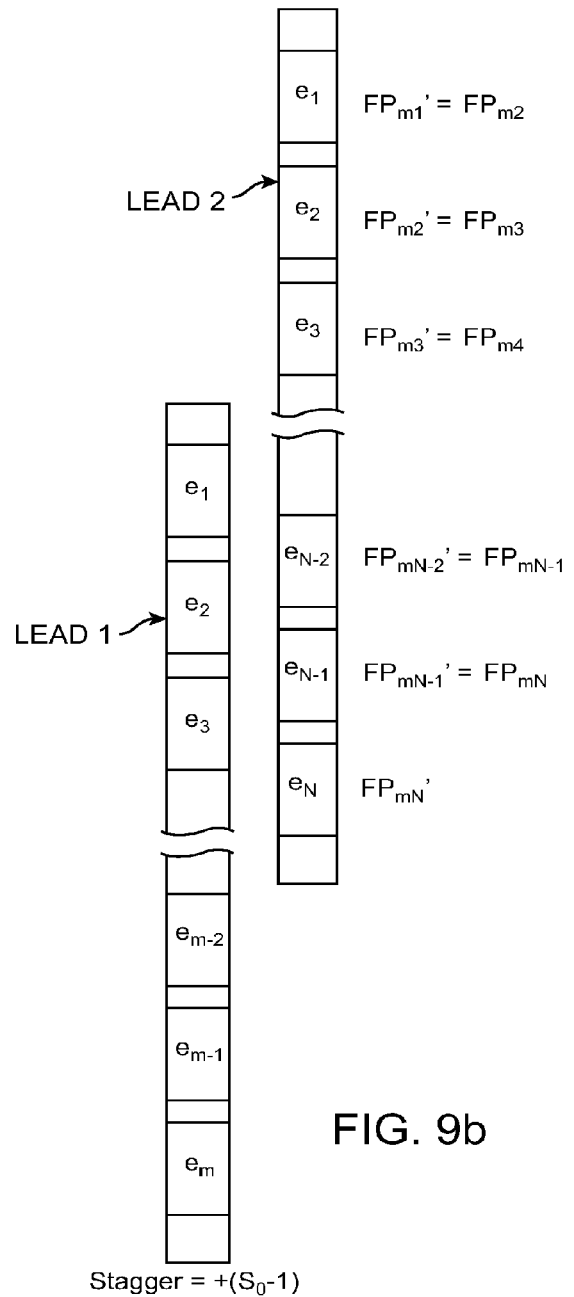
FIG. 9a
FIG. 9b

… (1)

SYSTEM FOR DETERMINING RELATIVE POSITION BETWEEN NEUROSTIMULATION LEADS

RELATED APPLICATION DATA

This application is a continuation of U.S. application Ser. No. 13/536,688, filed Jun. 28, 2012, now issued as U.S. Pat. No. 8,463,402, which is a continuation of U.S. application Ser. No. 12/550,136, filed Aug. 28, 2009, now issued as U.S. Pat. No. 8,233,992, which applications are herein incorporated by reference in their entirety.

FIELD OF THE INVENTION

The present invention relates to tissue stimulation systems, and more particularly, to apparatus and methods for determining the position of neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. Thus, electrical pulses can be delivered from the neurostimulator to the stimulation leads to stimulate the tissue and provide the desired efficacious therapy to the patient. The neurostimulation system may further comprise a handheld patient programmer in the form of a remote control (RC) to remotely instruct the neurostimulator to generate electrical stimulation pulses in accordance with selected stimulation parameters. The RC may, itself, be programmed by a clinician, for example, by using a clinician's programmer (CP), which typically includes a general purpose computer, such as a laptop, with a programming software package installed thereon.

In the context of an SCS procedure, one or more stimulation leads are introduced through the patient's back into the epidural space, such that the electrodes carried by the leads are arranged in a desired pattern and spacing to create an electrode array. One type of commercially available stimulation leads is a percutaneous lead, which comprises a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two or more percutaneous leads are placed down the respective sides of the midline of the spinal cord, and if a third lead is used, down the midline of the special cord. After proper placement of the stimulation leads at the target area of the spinal cord, the leads are anchored in place at an exit site to prevent movement of the stimulation leads. To facilitate the location of the neurostimulator away from the exit point of the stimulation leads, lead extensions are sometimes used.

The stimulation leads, or the lead extensions, are then connected to the IPG, which can then be operated to generate electrical pulses that are delivered, through the electrodes, to the targeted tissue, and in particular, the dorsal column and dorsal root fibers within the spinal cord. The stimulation creates the sensation known as paresthesia, which can be characterized as an alternative sensation that replaces the pain signals sensed by the patient. Intra-operatively (i.e., during the surgical procedure), the neurostimulator may be operated to test the effect of stimulation and adjust the parameters of the stimulation for optimal pain relief. The patient may provide verbal feedback regarding the presence of paresthesia over the pain area, and based on this feedback, the lead positions may be adjusted and re-anchored if necessary. A computer program, such as Bionic Navigator®, available from Boston Scientific Neuromodulation Corporation, can be incorporated in a clinician's programmer (CP) (briefly discussed above) to facilitate selection of the stimulation parameters. Any incisions are then closed to fully implant the system. Post-operatively (i.e., after the surgical procedure has been completed), a clinician can adjust the stimulation parameters using the computerized programming system to re-optimize the therapy.

Multi-lead configurations have been increasingly used in electrical stimulation applications (e.g., neurostimulation, cardiac resynchronization therapy, etc.). In the neurostimulation application of SCS, the use of multiple leads increases the stimulation area and penetration depth (therefore coverage), as well as enables more combinations of anodic and cathodic electrodes for stimulation, such as transverse multi-polar (bipolar, tripolar, or quadra-polar) stimulation, in addition to any longitudinal single lead configuration.

Several studies have demonstrated the advantage of using narrowly spaced, parallel leads placed symmetrically on both sides of the physiological midline in improving penetration and paresthesia coverage (see J. J. Struijk and J. Holsheimer, *Tripolar Spinal Cord Stimulation: Theoretical Performance of a Dual Channel System, Medical and Biological Engineering and Computing*, Vol. 34, No. 4, 1996, pp. 273-279; J. Holsheimer, B. Nuttin, G. King, W. Wesselink, J. Gybels, and P. de Sutter, *Clinical Evaluation of Paresthesia Steering with a New System for Spinal Cord Stimulation*, Neurosurgery, Vol. 42, No. 3, 1998, pp. 541-549; Holsheimer J., Wesselink, W. A., *Optimum Electrode Geometry for Spinal Cord Stimulation: the Narrow Bipole and Tripole, Medical and Biological Engineering and Computing*, Vol. 35, 1997, pp. 493-497).

The efficacy of SCS is related to the ability to stimulate the spinal cord tissue corresponding to evoked paresthesia in the region of the body where the patient experiences pain. Thus, the working clinical paradigm is that achievement of an effective result from SCS depends on the neurostimulation lead or leads being placed in a location (both longitudinal and lateral)

relative to the spinal tissue such that the electrical stimulation will induce paresthesia located in approximately the same place in the patient's body as the pain (i.e., the target of treatment). If a lead is not correctly positioned, it is possible that the patient will receive little or no benefit from an implanted SCS system. Thus, correct lead placement can mean the difference between effective and ineffective pain therapy.

When lead migration occurs, proper paresthesia coverage can most often be recaptured by reprogramming the IPG, e.g., by using the Bionic Navigator® software. When multiple percutaneous leads are used, programming of the IPG often requires the knowledge of the relative positions between the leads in order to properly place the poles of the generated electrical field. Such information, however, is not readily available to the programmer unless fluoroscopic imaging is performed. Fluoroscopic imaging involves ionized radiation, adds time and cost, and requires a bulky instrument, both of which may limit its use in the clinical setting, and effectively prevent its use outside of the clinical setting. If such lead placement is not detected in a timely manner before the system is fully implanted, it may result in inefficient therapy and possibly require a second surgery for lead revision. Thus, lead migration continues to be the most common technical complication of spinal cord stimulation therapy. A literature review suggested the incident rate of lead migration was approximately 13.2% (see T. Cameron, *Safety and Efficacy of Spinal Cord Stimulation for the Treatment of Chronic Pain: a 20-Year Literature Review*, J Neurosurg: Spine 2004, 100: 254-267).

Currently, the relative positions of multiple leads can be electronically estimated by measuring electrical signals between lead electrodes. For example, the Bionic Navigator® software uses an Electronically Generated Lead (EGL) Scan that estimates the relative lead positions by examining the profiles of electrical field potential measured from the electrodes that is generated due to the current flow in the medium. In particular, the EGL scan feature detects the stagger of the leads by comparing the profile of measured cross-lead field potentials with those calculated from a Finite Element Model (FEM) for known lead configurations. The FEM model provides a prediction of the field potentials that are expected to be measured on the electrodes, and it takes into account the geometric properties and electrical behaviors of the various elements in the spinal cord, as well as the boundary conditions imposed on the field potentials generated in the human body. The lead stagger can be determined by comparing the profile of the measured cross-lead field potentials with those computed from the FEM model for several known lead configurations. The lead configuration for which the modeled field potential profile best matches the measured field potential profile is designated as the detected lead configuration.

This technology provides an automated means to obtain the information about the relative position of implanted leads without using fluoroscopy. Such information may be used to increase programming accuracy, thus improving the patient outcomes and treatment efficacy. Although the comparison of the measured field potential profile to numerous reference profiles generated by the FEM model is computationally intensive and requires a lot of memory, the CP is embodied in a computer with the processing power and memory necessary to efficiently perform these computations.

As the next generation SCS systems are expected to give the patient more control over their stimulation programs to improve the therapy, as well as to reduce the need for office visits, it has been proposed to incorporate more programming features (previously reserved for CPs) into RCs and IPGs. Just as in the programming of the IPG through a CP, it is also desirable to have the capability of electronically determining the relative lead positions within the RC, which may be needed to properly program the IPG. However, in the case of the EGL Scan feature, the known field potential profiles to which the measured cross-lead field potentials are compared to determine the lead stagger is stored in a database that is loaded during the EGL Scan processing. This presents a potential difficulty in transferring the present EGL Scan features directly into a RC, because it requires memory space for the database storage that may not be available in the RC.

There, thus, remains a need for a technique that determines the relative positions of leads without requiring a large amount of memory space.

SUMMARY OF THE INVENTION

In accordance with a first aspect of the present invention, a method of operating two electrode leads disposed adjacent tissue (e.g., spinal cord tissue) of a patient is provided. The method comprises measuring a plurality of cross-lead electrical parameters (e.g., a field potential of a generated electrical field) to generate a measured electrical profile of the electrode leads (e.g., by activating at least one electrode carried by one of the leads to generate an electrical field within the tissue, and measuring an amplitude of the electrical parameter in response to the generated electrical field at each of a plurality of electrodes carried by another of the leads).

The method further comprises estimating a plurality of cross-lead electrical parameters to generate a first reference electrical profile for the electrode leads in a first known staggered configuration (e.g., by modeling an electrical field generated at an electrode carried by the one lead, and estimating amplitudes of the electrical parameter at a first set of the electrodes carried by the other lead using the modeled electrical field. The method further comprises spatially shifting the first reference electrical profile to generate a second reference electrical profile for the electrode leads in a second known staggered configuration (e.g., by shifting the estimated amplitudes from the first set of electrodes to a second set of the electrodes carried by the other lead, and estimating an amplitude of the electrical parameter at an end one of the electrodes carried by the other lead using the modeled electrical field.

The method further comprises comparing the measured electrical profile to the first and second reference electrical profiles. To provide a real-time analysis and to minimize storage space, the second reference electrical profile may be generated subsequent to comparing the measured electrical profile to the first reference electrical profile. In one method, the first and second lead stagger configurations are offset from each other by one center-to-center electrode spacing, and the estimated plurality of cross-lead electrical parameters is spatially shifted by one center-to-center electrode spacing. In this case, the method may further comprise estimating another plurality of cross-lead electrical parameters to generate a third reference electrical profile for the electrode leads in a third known staggered configuration offset from the first known staggered configuration a distance less than one center-to-center electrode spacing, spatially shifting the other estimated plurality of cross-lead electrical parameters the single electrode spacing to generate a fourth reference electrical profile for the electrode leads in a fourth known staggered configuration that is offset from the third known staggered configuration by one center-to-center electrode spacing, and comparing the measured electrical profile to the first, second, third, and fourth reference electrical profiles.

The method further comprises quantifying a longitudinal stagger between the electrode leads based on the comparison. In one method, the known stagger configuration corresponding to the known electrical profile that best matches the measured electrical profile is selected as the quantified longitudinal stagger. In an optional method, a graphical representation of the leads with the quantified longitudinal stagger is displayed. In another optional method, a neurostimulator is programmed with a plurality of stimulation parameters based on the quantified longitudinal stagger.

An optional method comprises estimating additional pluralities of cross-lead electrical parameters to respectively generate an additional plurality of reference electrical profiles for the electrode leads in an additional plurality of known staggered configurations offset from each other by a distance less than one center-to-center electrode spacing, comparing the measured electrical profile to the additional reference electrical profiles, and quantifying the longitudinal stagger between the electrode leads based on the comparison between the measured electrical profile and the first, second, and additional reference electrical profiles. The distance that the additional known staggered configurations are offset from each other may be, e.g., predetermined or may be dynamically selected based on the comparison between the measured electrical profile and at least some of the additional reference electrical profiles.

In accordance with a second aspect of the present inventions, a neurostimulation control system for use with electrode leads is provided. The neurostimulation control system comprises a user interface configured for receiving an input from a user. The neurostimulation control system further comprises a processor configured for generating instructions to measure a plurality of cross-lead electrical parameters, generating a measured electrical profile of the electrode leads from the measured cross-lead electrical parameters, estimating a plurality of cross-lead electrical parameters to generate a first reference electrical profile for the electrode leads in a first known staggered configuration, spatially shifting the first reference electrical profile to generate a second reference electrical profile for the electrode leads in a second known staggered configuration, comparing the measured electrical profile to the first and second reference electrical profiles, and quantifying a longitudinal stagger between the electrode leads based on the comparison. The details of these processor functions can be the same as those described above with respect to the method. The external control device may further comprise a display for displaying the leads with the quantified longitudinal stagger. The neurostimulation control system may comprise an external control device containing the user interface and at least one processor. In this case, the neurostimulation control system may further comprise telemetry circuitry configured for wirelessly transmitting the instructions to a neurostimulator to measure the plurality of cross-lead electrical parameters. Alternatively, at least some of the processing capability can be incorporated into the neurostimulation device itself.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 9a and 9b are plan views showing a "shifting" scheme used by the RC of the SCS system of FIG. 1 to translate field potential values from the electrodes of one known lead stagger configuration to another known lead stagger configuration;

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a multi-lead system such as a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
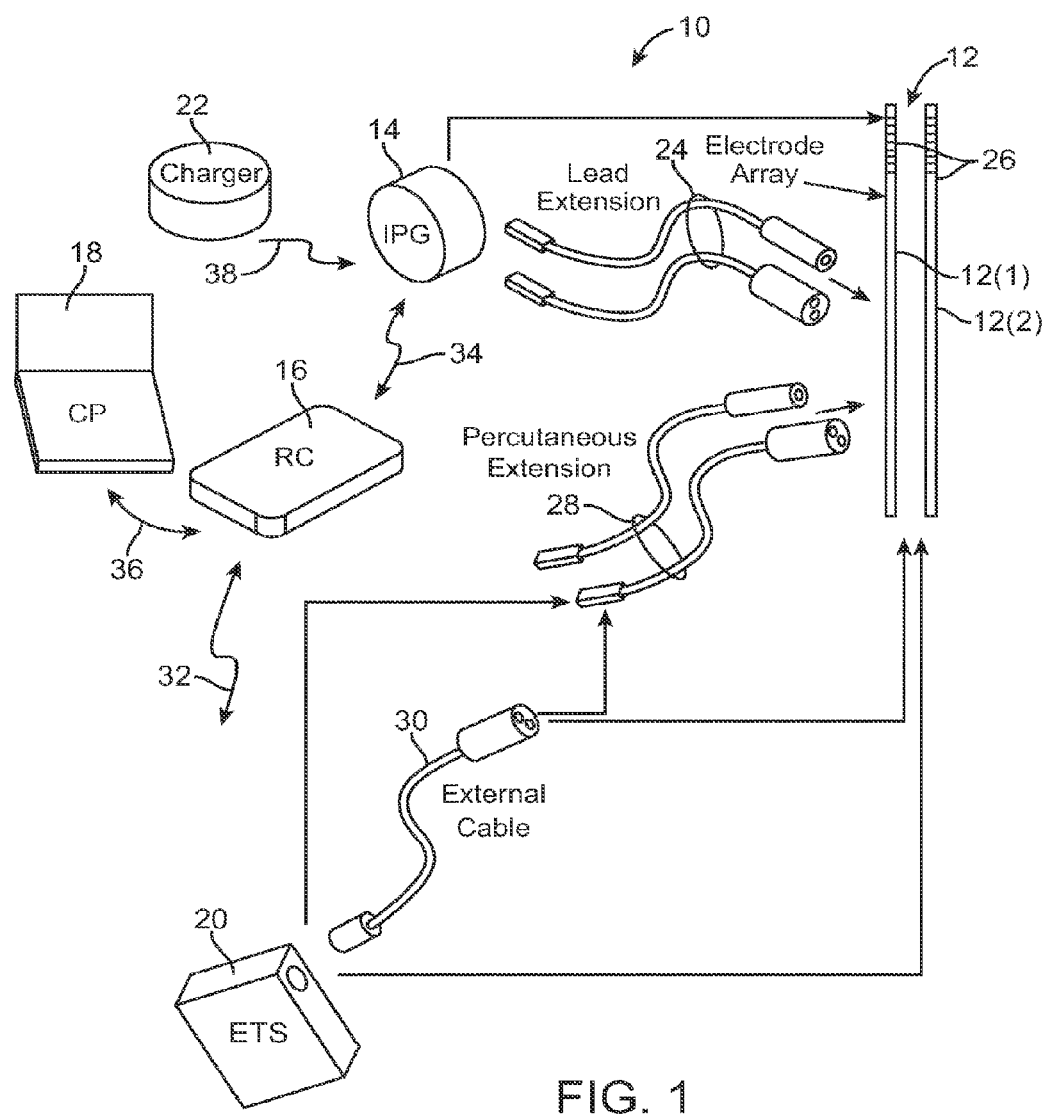
FIG. 1 is plan view of one embodiment of a spinal cord stimulation (SCS) system arranged in accordance with the present inventions.

Turning first to FIG. 1, an exemplary SCS system 10 generally comprises a plurality of percutaneous leads 12 (in this case, two percutaneous leads 12(1) and 12(2)), an implantable pulse generator (IPG) 14, an external remote control (RC) 16, a Clinician's Programmer (CP) 18, an External Trial Stimulator (ETS) 20, and an external charger 22.

The IPG 14 is physically connected via two lead extensions 24 to the stimulation leads 12, which carry a plurality of electrodes 26 arranged in an array. As will be also described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters. The IPG 14 and stimulation leads 12 can be provided as an implantable neurostimulation kit, along with, e.g., a hollow needle, a stylet, a tunneling tool, and a tunneling straw. Further details discussing implantable kits are disclosed in U.S. Application Ser. No. 61/030,506, entitled "Temporary Neurostimulation Lead Identification Device," which is expressly incorporated herein by reference.

The ETS 20 may also be physically connected via percutaneous lead extensions 28 or external cable 30 to the stimulation lead 12. The ETS 20, which has similar pulse generation circuitry as the IPG 14, also delivers electrical stimulation energy in the form of a pulse electrical waveform to the electrode array 26 in accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation lead 12 is implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
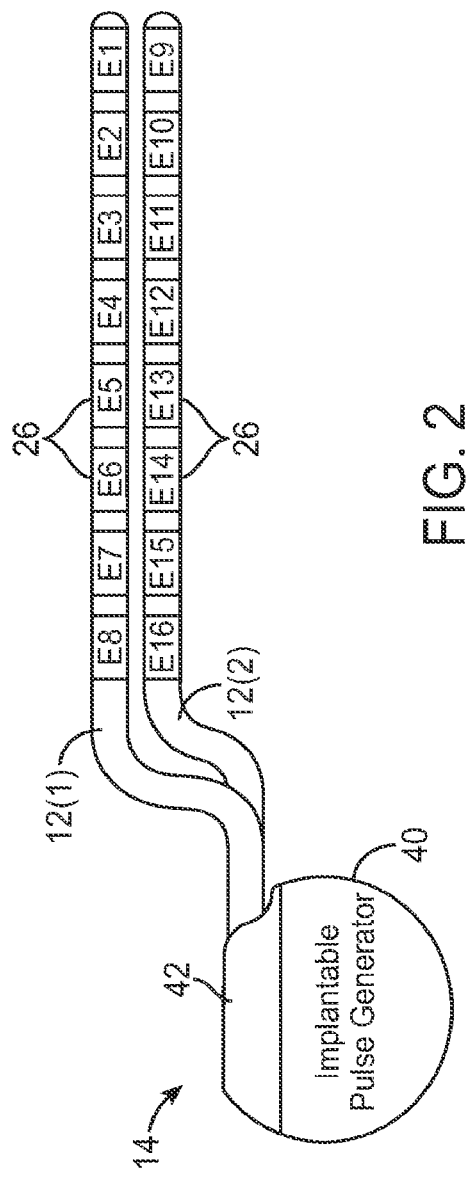
FIG. 2 is a plan view of an implantable pulse generator (IPG) and another embodiment of a percutaneous stimulation lead used in the SCS system of FIG. 1.

Referring now to FIG. 2, the external features of the stimulation leads 12 and the IPG 14 will be briefly described. Each of the stimulation leads 12 has eight electrodes 26 (respectively labeled E1-E8 and E9-E16). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565, 547, entitled "Cylindrical Multi-Contact Electrode Lead for Neural Stimulation and Method of Making Same," the disclosures of which are expressly incorporated herein by reference.

The IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the stimulation leads 12 mate in a manner that electrically couples the electrodes 26 to the internal electronics (described in further detail below) within the outer case 40. To this end, the connector 42 includes two ports (not shown) for receiving the proximal ends of the three percutaneous leads 12. In the case where the lead extensions 24 are used, the ports may instead receive the proximal ends of such lead extensions 24.

As will be described in further detail below, the IPG 14 includes pulse generation circuitry that provides electrical stimulation energy to the electrodes 26 in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), pulse rate (measured in pulses per second), and pulse shape.

With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Figure 3:
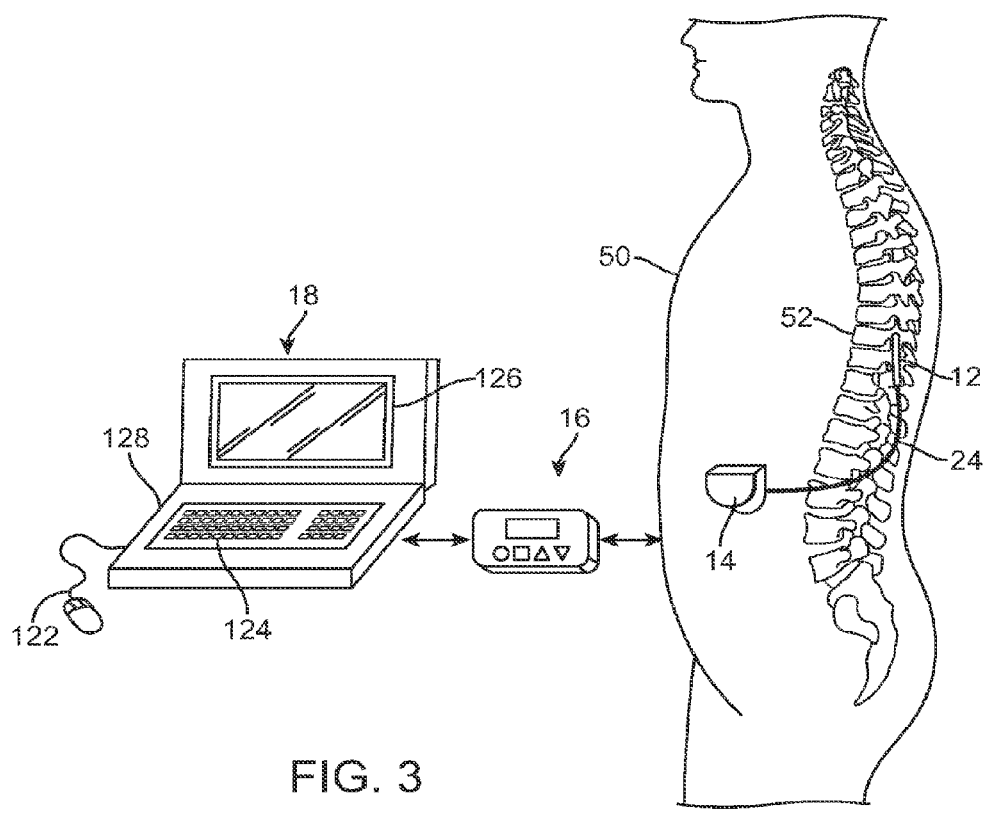
FIG. 3 is a plan view of the SCS system of FIG. 1 in use with a patient.

Referring to FIG. 3, the stimulation leads 12 are implanted within the spinal column 46 of a patient 48. The preferred placement of the stimulation leads 12 is adjacent, i.e., resting near, or upon the dura, adjacent to the spinal cord area to be stimulated. Due to the lack of space near the location where the stimulation leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the stimulation leads 12. As there shown, the CP 18 communicates with the IPG 14 via the RC 16. While the stimulation leads 12 are illustrated as being implanted near the spinal cord area of a patient, the stimulation leads 12 may be implanted anywhere in the patient's body, including a peripheral region, such as a limb, or the brain. After implantation, the IPG 14 is used to provide the therapeutic stimulation under control of the patient.

Figure 4:
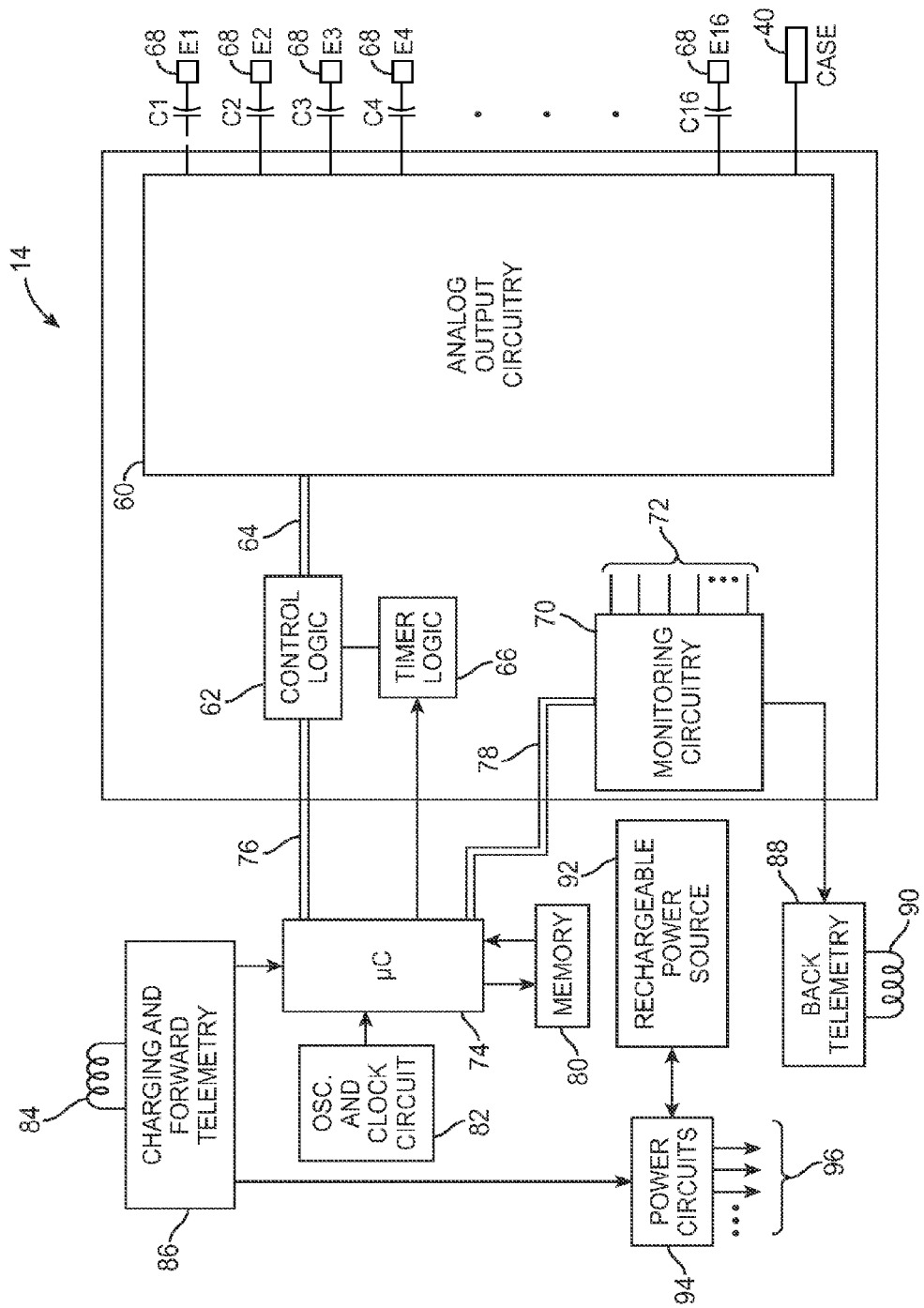
FIG. 4 is a block diagram of the internal components of the IPG of FIG. 1.

Turning next to FIG. 4, the main internal components of the IPG 14 will now be described. The IPG 14 includes stimulation output circuitry 60 configured for generating electrical stimulation energy in accordance with a defined pulsed waveform having a specified pulse amplitude, pulse rate, pulse width, pulse shape, and burst rate under control of control logic 62 over data bus 64. Control of the pulse rate and pulse width of the electrical waveform is facilitated by timer logic circuitry 66, which may have a suitable resolution, e.g., 10 μs. The stimulation energy generated by the stimulation output circuitry 60 is output via capacitors C1-C16 to electrical terminals 68 corresponding to the electrodes 26.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., power supply voltages, temperature, battery voltage, and the like. Notably, the electrodes 26 fit snugly within the epidural space of the spinal column, and because the tissue is conductive, electrical measurements can be taken from the electrodes 26. Significantly, the monitoring circuitry 70 is configured for taking such electrical measurements, so that, as will be described in further detail below, the RC 16 and CP 18 can automatically determine the relative positioning between the leads 12. In the illustrated embodiment, the electrical measurements taken by the monitoring circuitry 70 for the purpose of determining the relative positioning of the leads 12, are field potentials or other electrical parameters (e.g., current and/or impedance) that may be used to derive the field potential. The monitoring circuitry 70 may also measure impedance at each electrode 26 in order to determine the coupling efficiency between the respective electrode 26 and the tissue and/or to facilitate fault detection with respect to the connection between the electrodes 26 and the analog output circuitry 60 of the IPG 14.

Electrical data can be measured using any one of a variety means. For example, the electrical data measurements can be made on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the electrical data measurements can be made independently of the electrical stimulation pulses, such as described in U.S. Pat. Nos. 6,516,227 and 6,993,384, which are expressly incorporated herein by reference.

The IPG 14 further comprises processing circuitry in the form of a microcontroller 74 that controls the control logic 62 over data bus 76, and obtains status data from the monitoring circuitry 70 via data bus 78. The microcontroller 74 additionally controls the timer logic 66. The IPG 14 further comprises memory 80 and an oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and parameters. In controlling the operation of the IPG 14, the microcontroller 74 is able to individually generate electrical pulses at the electrodes 26 using the analog output circuitry 60, in combination with the control logic 62 and timer logic 66, thereby allowing each electrode 26 to be paired or grouped with other electrodes 26, including the monopolar case electrode, and to control the polarity, amplitude, rate, and pulse width through which the current stimulus pulses are provided.

The IPG 14 further comprises an alternating current (AC) receiving coil 84 for receiving programming data (e.g., the operating program and/or stimulation parameters) from the RC 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data (including the field potential and impedance data) sensed through the monitoring circuitry 70 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits) received by the AC receiving coil 84. To recharge the power source 92, an external charger (not shown), which generates the AC magnetic field, is placed against, or otherwise adjacent, to the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

It should be noted that the diagram of FIG. 4 is functional only, and is not intended to be limiting. Those of skill in the art, given the descriptions presented herein, should be able to readily fashion numerous types of IPG circuits, or equivalent circuits, that carry out the functions indicated and described. It should be noted that rather than an IPG for the neurostimulator, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
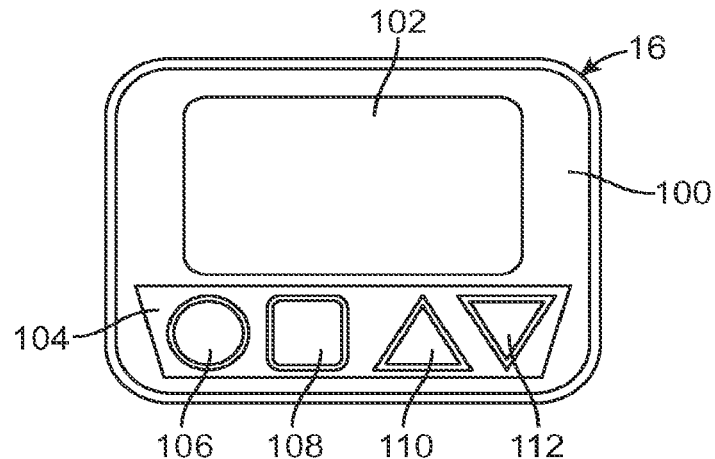
FIG. 5 is a plan view of a remote control that can be used in the SCS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can be actuated to increase or decrease any of stimulation parameters of the pulse generated by the IPG 14, including pulse amplitude, pulse width, and pulse rate.

Figure 6:
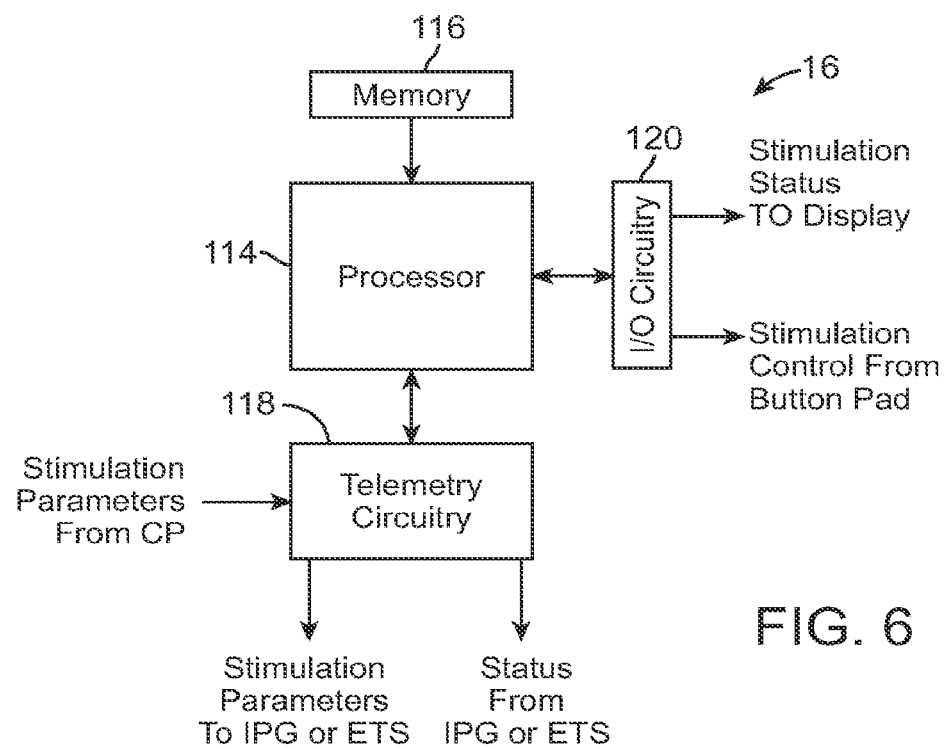
FIG. 6 is a block diagram of the internal componentry of the remote control of FIG. 5.

Referring to FIG. 6, the internal components of an exemplary RC 16 will now be described. The RC 16 generally includes a processor 114 (e.g., a microcontroller), memory 116 that stores an operating program for execution by the processor 114, and telemetry circuitry 118 for transmitting control data (including stimulation parameters and requests to provide status information) to the IPG 14 (or ETS 20) and receiving status information (including the measured electrical data) from the IPG 14 (or ETS 20) via link 34 (or link 32) (shown in FIG. 1), as well as receiving the control data from the CP 18 and transmitting the status data to the CP 18 via link 36 (shown in FIG. 1). The RC 16 further includes input/output circuitry 120 for receiving stimulation control signals from the button pad 104 and transmitting status information to the display screen 102 (shown in FIG. 5). Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 3, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters.

Figure 7:
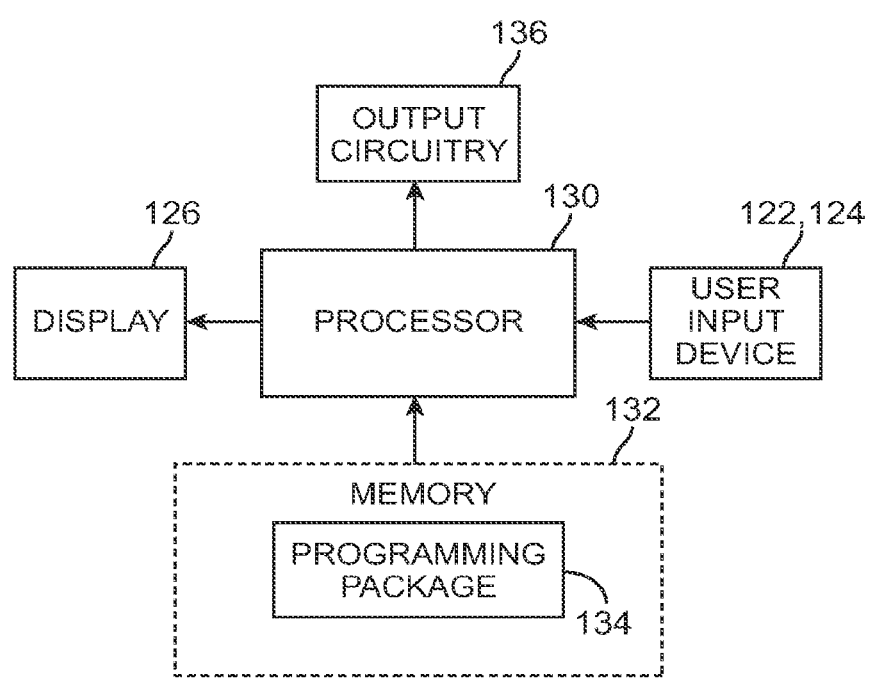
FIG. 7 is a block diagram of the components of a clinician's programmer that can be used in the SCS system of FIG. 1.

To allow the clinician to perform these functions, the CP 18 includes a mouse 121, a keyboard 122, and a programming display screen 124 housed in a case 126. It is to be understood that in addition to, or in lieu of, the mouse 121, other directional programming devices may be used, such as a joystick, or directional keys included as part of the keys associated with the keyboard 122. As shown in FIG. 7, the CP 18 generally includes a processor 128 (e.g., a central processor unit (CPU)) and memory 130 that stores a stimulation programming package 132, which can be executed by the processor 128 to allow a clinician to program the IPG 14 (or ETS 20) and RC 16. The CP 18 further includes telemetry circuitry 134 for downloading stimulation parameters to the RC 16 and uploading stimulation parameters already stored in the memory 116 of the RC 16 via link 36 (shown in FIG. 1). The telemetry circuitry 134 is also configured for transmitting the control data (including stimulation parameters and requests to provide status information) to the IPG 14 (or ETS 20) and receiving status information (including the measured electrical data) from the IPG 14 (or ETS 20) indirectly via the RC 16.

The CP 18 is configured for automatically determining the relative positioning (e.g., the stagger, separation and/or tilt angle) of the percutaneous leads 12 by taking one or more cross-lead electrical field measurements and comparing these measurements to reference electrical field measurements of known lead configuration to determine the relative position between two leads. In the embodiment described below, field potential measurements are taken, although other types of measurements, such as impedance measurements, can alternatively be taken. Because the CP 18 has a relatively high processing power and storage capability, the CP 18 may use conventional means, such as that discussed in the background of the invention, to determine the relative positioning of the leads 12.

The CP 18 accomplishes this function by measuring electrical field potentials on a number of electrodes on one lead 12 in response to electrical current sourced by electrodes on another lead 12. In particular, it is known that current flow in a conductive medium due to the presence of a current source is accompanied (associated) with a potential electrical field.

Figure 8A:
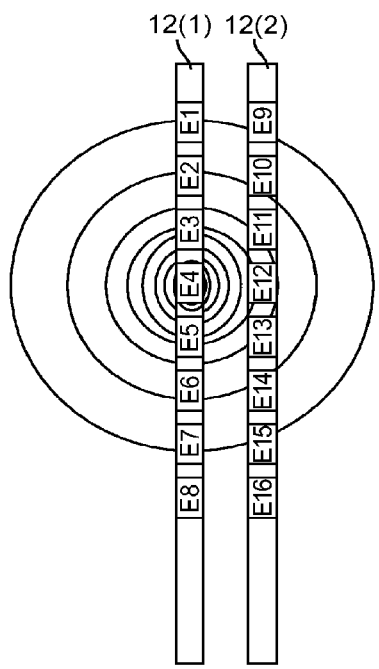
FIGS. 8a and 8b are views of a pair of electrode leads used in the SCS system of FIG. 1 and corresponding measured field potential profiles, wherein one lead is used to source electrical current and another lead is used to measure an electrical field potential.
Figure 8A:
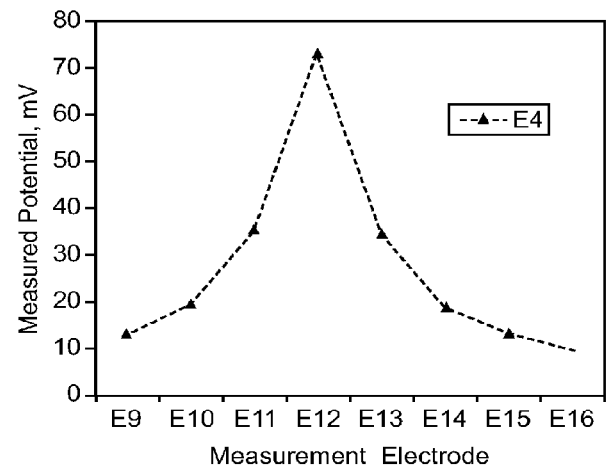
Figure 8B:
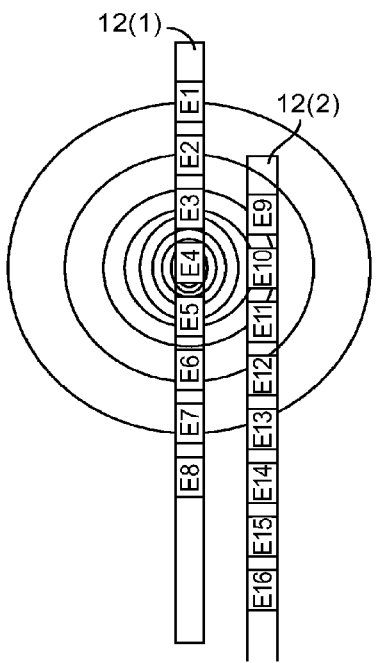
Figure 8B:
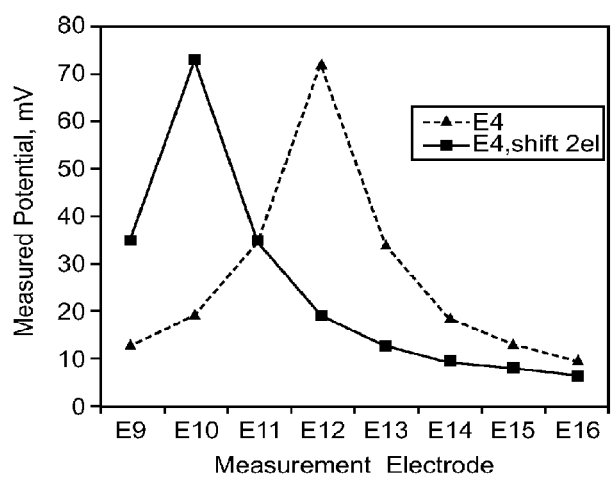

As an example, for a point current source, the electrical field potential relates to the source current as:

$$\Phi = \frac{I}{4\pi\sigma r}, \quad [1]$$

where ϕ is the field potential, σ is the conductivity of the medium, r is the distance to the point source, and/is the applied source current. In general, for a monopolar case, the field potential (absolute value) decreases with increasing distance from the current source. In a system of multipolar leads 12(1), 12(2) (as shown in FIGS. 8a and 8b), a series of monopolar field potential measurements can be performed by sourcing the current from each one of the electrodes (e.g., the electrodes on lead 12(1)), and measuring the field potential on all other non-active electrodes (e.g., the electrodes on lead 12(2)). The field potential measured on each electrode will follow the general relationship with the distance, with the electrode closest to the source having the highest field potential. It should be noted that while a point source model is only used here as an example, more complicated models, such as a Finite Element Model (FEM) or other mathematical models can also be used to describe the relationship between the field potential and the distance between source and measurement electrodes.

It is the field potentials measured from the cross-lead (i.e., the lead other than the one containing the source electrode) electrodes that contain the information about the relative lead position. When current is sourced on one electrode, the field potential measured on the cross-lead electrodes will indicate the pattern with the highest field potential likely measured on the electrode closest to the source electrode, and gradually decreased field potential measured on both sides along the lead. For example, the diagrams illustrated in FIGS. 8a and 8b show the cross-lead field potential profiles associated with known lead positions. FIG. 8a shows a baseline case when both leads 12(1), 12(2) are perfectly aligned. The source contact is electrode E4 and the closest to the source electrode E4 is electrode E12, and thus, the peak field potential is measured on electrode E12. If the leads are staggered (e.g., staggered by two electrodes as illustrated in FIG. 8b)), the cross-lead electrode closest to the source electrode E4 now becomes electrode E10, and thus, the peak field potential measured along the lead is also shifted by two electrodes, as compared to the baseline. Such shifting in the field potential profile provides a featuring pattern that allows for the estimation of the relative lead stagger.

Based on the distance-potential relationship, the profile of the field potentials expected to be measured on the cross-lead electrodes may be predicted for a known lead stagger and stored in the memory 132 of the CP 18 as a look-up table containing the modeled field potential profiles and corresponding lead stagger configurations. In the illustrated embodiment, the CP 18 may utilize a numerical integration model (e.g., FEM) to predict these field potential profiles. The field potential profile measured on the cross-lead electrodes for a particular lead stagger can then be examined for its similarity/correlation to those of known lead staggers to estimate the actual lead stagger. Correlation analysis (e.g., Pearson or Spearman) can be used to evaluate the similarity/correlation. In this case, the detected lead stagger is designated as the one for which the modeled field potential profiles has the maximum correlation with the measured field potentials.

Because the RC 16 has a limited processing power and storage capability, the FEM used to generate the modeled field potentials, which is computationally intensive and requires massive storage space, may not be implemented in the RC 16. Instead, the processor 114 of the RC 16 utilizes an efficient means for determining the relative positioning of the leads 12 by sequentially generating reference field potential profiles for various stagger positions in real-time using analytical models, as well as a "shifting" scheme and "sweeping" strategy described in further detail below, and comparing these reference profiles as they are generated to a previously measured field potential profile. As such, the RC 16 need only store the measured field potential profile and one reference field potential profile at a time, thereby substantially decreasing the memory storage space.

The RC 16 accomplishes this by first instructing the IPG 16 (i.e., the monitoring circuitry 70 shown in FIG. 4) to measure cross-lead electrical parameters (in this case, field potentials) in a conventional manner to generate a measured electrical profile of the leads 12. In particular, a source electrode carried by the first lead 12(1) (e.g., electrode E4) is activated to generate a source electrical current, and an amplitude of the field potential is measured in response to the generated source current at each of measurement electrodes carried by the second lead 12(2) (e.g., each of electrodes E9-E16). Other source electrodes on the first lead 12(1) (e.g., electrodes E1-E3 and E5-E8) can also be used to generate the source electrical currents, and each of the measurement electrodes carried by the second lead 12(2) (e.g., electrodes E9-E16) can be used to measure the respective generated source currents.

Thus, a measured field potential profile having an M×N number of data points can be generated, where M is the number of source electrodes used to generate a source electrical current, and N is the number of measurement electrodes used to measure the field potential in response to the sourced current. In the exemplary case where the first lead 12(1) carries electrodes E1-E8 and the second lead 12(2) carries electrodes E9-E16, the field potential profile may have M×N=64 data points. To provide redundancy, or alternatively, the electrodes on the second lead 12(2) can be used to generate source electrical currents, and the electrodes on the first lead 12(1) can be used to measure the amplitudes of the field potentials in response to the source electrical currents. In any event, the measured field potential profile can then wirelessly transmitted from the IPG 14 to the RC 16 where it can be stored in the memory 116 (shown in FIG. 6).

The RC 16 then estimates cross-lead electrical parameters (in this case, cross-lead field potentials) using a "shifting" scheme to generate reference electrical profile for the electrode leads in various known lead stagger configurations. In particular, the RC 16 generates an initial reference field potential profile for an initial lead stagger configuration by modeling an electrical field generated in response to the sourced electrical current at an electrode carried by the first lead 12(1) (e.g., electrode E4), and estimating the amplitudes of the field potentials at each of the electrodes carried by the second lead 12(2) (e.g., electrodes E9-E16) using the modeled electrical field. The initial known lead stagger configuration that is modeled can be a lead stagger configuration with no stagger, as shown in FIG. 8a. As will be described in further detail below, the initial reference field potential profile can then be spatially shifted to generate other reference field potential profiles.

In the illustrated embodiment, the electrical field is analytically modeled to approximate the output from an FEM using an explicit mathematical equation, which provides a simple and straightforward way to produce the modeled data.

In this case, the analytical model describes the monopolar field potential as a function of the two-dimensional (x, y) position of the measurement electrode relative to the source electrode (i.e., transverse and longitudinal distance between the source and measurement electrodes), and is an optimal curve fit to the FEM field potential in the sense of Least Squared Error (LSE). The target field potentials were obtained from an FEM of parallel percutaneous leads, as described in Lee D., Moffitt M. Bradley K., Peterson D., *Selective Neural Activation by Field Sculpting: Results From a New Computer Model for Spinal Cord Stimulation*, 16$^{th}$ Annual Computational Neuroscience Meeting, Jul. 7-12, 2007, Toronto, Canada: 177.

The optimal curve fit can be obtained in the form of:

$$FP = \frac{l}{sqrt(\sigma_x x^{k_x} + \sigma_y y^{k_y})} + C\exp(-\tau y^2), \quad [2]$$

where l, $\sigma_x$, $\sigma_y$, $k_x$, $k_y$, C, and $\tau$ are free parameters, and x and y are transverse and longitudinal distance between the source and measurement electrodes. One set of free parameters that gives an optimal curve fit to the FEM is: l=149.5437, $\sigma_x$=7.8359, $\sigma_y$=0.118942, $k_x$=0.476833, $k_y$=2.757028, C=57.9078, and $\tau$=0.0002945. Thus, using equation [2], the expected field potential at each measurement electrode (i.e., amplitudes of the field potentials at the measurement electrodes) can be computed for any given source electrode to generate reference field potential profiles for known lead stagger configurations. Notably, the form of the model equation will depend on the lead geometry and the tissue medium that are to be modeled.

Significantly, a "shifting" scheme is used to generate reference field potential profiles for additional known lead stagger configurations in a computationally efficient manner. This "shifting" scheme is based on the fact that when one multipolar lead (e.g., a lead of N contacts) is moved relative to another by an amount equal to the center-to-center distance between two adjacent electrodes, all electrodes, with the exception of the distal or proximal electrodes, will resume the positions of their neighboring electrodes. Thus, the field potentials expected to be measured on each of these electrodes in the new lead stagger configuration will take the field potential values calculated for its neighboring electrode in the previous lead stagger configuration, which means that only the field potential for one end electrode is unknown and needs to be calculated using equation [2]. In some cases where field potential values may be determined via symmetry (i.e., if the field potential value for a symmetric position (relative to the source electrode) is available), no calculations are needed.

The "shifting" scheme thus generates a field potential profile for the new lead stagger configuration by spatially shifting the field potential profile previously computed using equation [2] for the leads in the previous lead stagger configuration. As will be described in further detail below, the field potential profile is spatially shifted by shifting the estimated amplitudes of the field potentials from a first set of measurement electrodes in the previous lead stagger configuration to a second set of measurement electrodes in the new lead stagger configuration, with the second electrode set being offset from the first electrode set by an n number of electrodes. That is, when the lead stagger is changed by an n number of electrodes, a subset of the electrodes in the new stagger configuration will take the same position relative to the source electrode as a subset of the electrodes in the previous stagger configuration, and will thus, assume the field potential values that were previously assigned to them. In the exemplary case described below, n=1 (i.e., a single electrode offset)), although the offset number n can be any number depending on the desired resolution of the lead stagger detection.

In the illustrated embodiment, only a subset of values in the previous field potential profile will be shifted to the new field potential profile, since the field potential value at one end of the lead will have to be removed, and the field potential at the other end of the lead will need to be amended. That is, because the field potential value associated with the last electrode (relative to the direction of lead shift) in the previous lead stagger configuration will not be needed for the new lead stagger configuration, this value will be removed from the new field potential profile. However, because the field potential value associated with the first electrode (relative to the direction of lead shift) in the new lead stagger configuration cannot be associated with a field value in the previous lead stagger configuration, this value will need to be computed using equation [2] (or using symmetry to estimate).

The shifting, removal, and amending of field potential values can best be explained with reference to FIGS. 9a and 9b. The field potential computation begins with the assumption that the two leads (Lead 1 and Lead 2) have an initial stagger. For example, for a lead of N contacts, it can be assumed that the initial stagger equals $S_0$ electrodes (with Lead 1 above Lead 2), as shown in FIG. 9a. For each of the M source configurations, the field potentials on each of the cross-lead electrodes (denoted as $FP_{m1}$, $FP_{m2}$, . . . $FP_{mN}$, where m=1, 2, . . . , M) can be evaluated using the analytical model defined by equation [2] based on the their distances from the source electrode $E_S$.

The position of Lead 2 can then be shifted by an amount equal to the center-to-center distance between two adjacent electrodes, and thus, the assumed lead stagger is changed by a full electrode center-to-center distance (i.e., stagger equals ($S_0$−1) electrodes), as shown in FIG. 9b. Thus, the field potentials of the new lead stagger configuration (denoted as $FP_{m1'}$, $FP_{m2'}$, . . . $FP_{mN-1'}$) will take the values of $FP_{m2}$, $FP_{m3}$, . . . $FP_{mN}$ previously computed for the initial lead stagger configuration. Only the field potential values denoted $FP_{mN'}$ (m=1, 2, . . . , M) will be unknown for the new lead stagger configuration, and will need to be computed using the analytical model defined by equation [2].

The "shifting" scheme thus produces the field potential profile for the new stagger configuration by shifting the field potential profile obtained from the previous lead stagger configuration, removing the first field potential value $FP_{m1}$, and amending the new field potential value $FP_{mN'}$ at the end. The field potential values on the cross-lead electrodes (i.e., electrodes on Lead 2), then become $FP_{m2}$, $FP_{m3}$, . . . $FP_{mN}$, $FP_{mN'}$, where m=1, 2, . . . , M. The lead stagger can be repeatedly changed by a full electrode center-to-center distance, and the shifting scheme performed for each new lead stagger configuration in order to generate additional reference field potential profiles.

Thus, it can be appreciated that this "shifting" scheme makes use of the field potential values that have already been computed using equation [2], thus significantly reducing the number of new computations needed for the new lead stagger configuration. For each lead stagger configuration, only a matrix of M×N (M is the number of source configurations, and N is the number of measurement electrodes) is needed to save the computed field potential profiles, and, except for the initial field potential profile computation, only M×1 field potential values need to be computed for each new lead stagger configuration.

It should be noted that in the case of two leads, moving one lead in one direction is equivalent to moving the other lead in the opposite direction. Thus, the cross-lead field potential data for the two leads will be shifted in opposite directions as well. In the example shown above, when Lead 2 is moving down, the field potential data profile for Lead 2 will be shifted by removing the first field potential value and amending the new field potential value at the last data entry while the field potential for Lead 1 will be shifted by removing the last field potential value and amending the new field potential value at the first data entry. In addition, switching the field potential profile for Lead 1 and Lead 2 will reverse the direction of stagger that is being evaluated (since stagger only represents the relative offset of one lead to the other lead). This interchangeability allows for the evaluation of two stagger positions (symmetric on two directions) using the same field potential profiles (one only needs to switch the lead assignment to each field potential profile).

The purpose of the "shifting" scheme is to make use of the field potentials that have already been computed, thereby reducing the number of new computations. The field potentials can be reused only if the lead stagger is shifted by a full electrode center-to-center distance (since one electrode will completely resume the position of its neighboring electrode). For a single round of shifting, this will only allow one to evaluate the lead stagger at a course resolution of a full electrode center-to-center distance. However, in clinical applications, it is expected that the lead stagger would be evaluated at a finer resolution.

To evaluate the lead stagger at a finer resolution, the RC 16 implements the "sweep" strategy in conjunction with the "shifting" scheme. The "sweep" approach evaluates the lead stagger in several rounds to fill gaps between the full electrode offsets to provide a finer resolution. In particular, in each round, the lead stagger is shifted using the afore-described "shifting" scheme repeatedly at a course resolution of one full electrode center-to-center distance. However, the initial stagger configuration in each round is offset by a smaller distance defined by the fine resolution. There are two approaches to achieve fine resolutions using the "sweep" strategy.

Figure 10A:
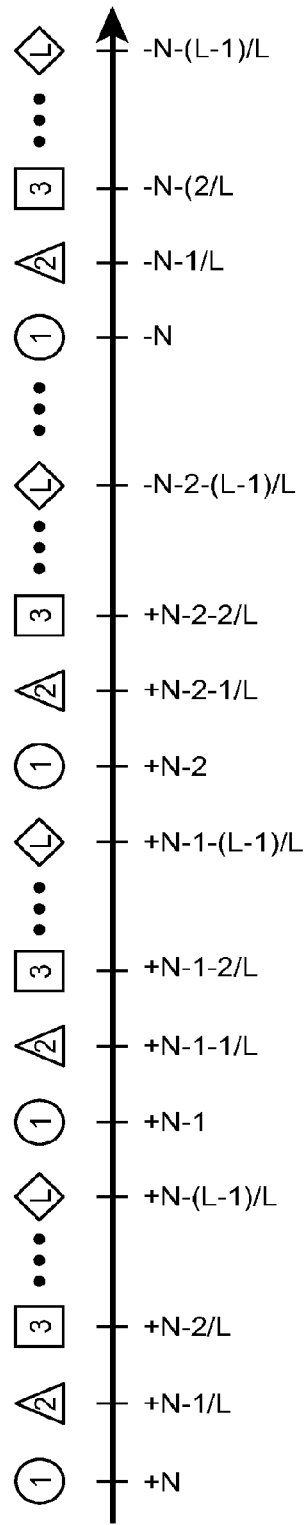
FIGS. 10a and 10b are plan views showing a "sweep" used in conjunction with the "shifting" scheme of FIGS. 9a and 9b to translate field potential values from the electrodes of one known lead stagger configuration to another known lead stagger configuration that are offset from each other by less than an electrode center-to-center spacing.

In the first type of "sweep" approach, the fine resolution is fixed and pre-defined, and in each round, except for the first, the initial stagger position is offset by the amount defined by the fine resolution (e.g., 1/L electrode center-to-center distance, where L is a fixed arbitrary number). As shown in FIG. 10a, in the first round (represented by the number "1"), the initial lead stagger configuration is set as +N electrode, and the lead staggers (shown as circles) are sequentially evaluated at +N, +N−1, +N−2, . . . , −N electrode using the "shifting" scheme discussed above. In the second round (represented by the number "2"), the initial lead stagger configuration is set as +N−1/L electrode, and the lead staggers (shown as triangles) are sequentially evaluated at +(N−1/L), +N−1−1/L, +N−2−1/L, . . . , −N−1/L electrode using the "shifting" scheme discussed above. In the third round (represented by the number "3"), the initial stagger configuration is set as +N−2L electrode, and the lead staggers (shown as squares) are sequentially evaluated at +N−2/L, +N−1−2/L, +N−2−2/L, . . . , −N−2/L electrode using the "shifting" scheme discussed above. In the last round (represented by the letter "L", the initial stagger configuration is set as +N−(L−1)/L), and the lead staggers (shown as diamonds) are sequentially evaluated at +N−(L−1)/L), +(N−1−(L−1)/L), +(N−2−(L−1)/L), . . . , −N−(L−1)/L) electrode using the "shifting" scheme discussed above.

Figure 10B:
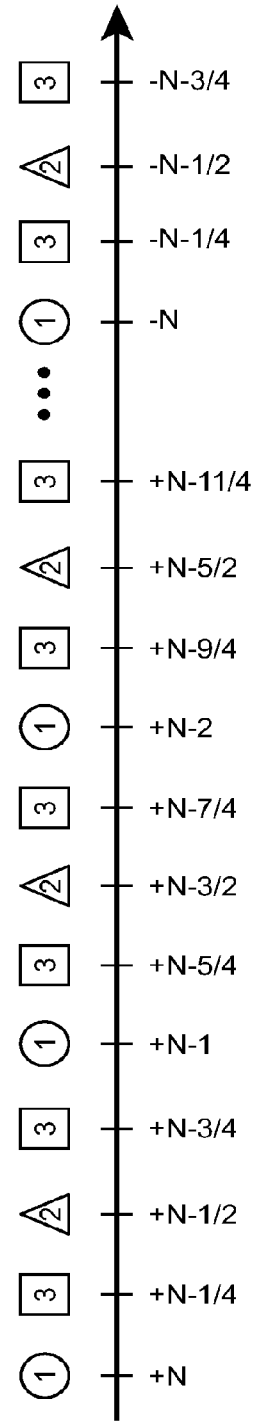

In the second type of "sweep" approach, the fine resolution is dynamic, and in each round, except for the first, the offset of the initial stagger position is cut in half for each round (e.g., $\frac{1}{2}^{K-1}$ electrode center-to-center distance, where K is the number of rounds). As shown in FIG. 10b, in the first round (represented by the number "1"), the initial lead stagger configuration is set as +N electrode, and the lead staggers (shown as circles) are sequentially evaluated at +N, +N−1, +N−2, . . . , −N electrode using the "shifting" scheme discussed above. In the second round (represented by the number "2"), the initial lead stagger configuration is offset by ½ electrode center-to-center distance, such that it is set to +(N−1/2) electrode, and the lead staggers (shown as triangles) are sequentially evaluated at +N−1/2, +N−3/2, +N−5/2, . . . , −N−1/2 electrode. The lead stagger configurations in this second round, together with those evaluated in the first round, will provide a resolution of ½ electrode center-to-center distance. In the third round (represented by the number "3"), the offset of the initial lead stagger configuration is cut in half again, such that two initial lead stagger configurations are set to +N−1/4 and +N−3/4, and the lead staggers (shown as squares) are sequentially evaluated at +N−1/4, +N−3/4, +N−5/4, +N−7/4, +N−9/4, +N−11/4, . . . , −N−1/4, −N−3/4. The lead stagger configurations in this third round, together with those evaluated in the previous rounds, will provide a resolution of ¼ electrode center-to-center distance. Such process can be repeated if needed to achieve higher resolution. The RC 16 can check the stagger detection results after each round of evaluation to determine if the current resolution is sufficient or a finer resolution is needed.

After each reference field potential profile is generated using the afore-described "shifting" scheme and "sweeping" strategy, the measured field potential profile is compared to the currently generated reference field potential profile. Advantageously, because each reference field potential profile is generated and compared to the measured field potential profile in real-time, only a minimal amount of memory required, since the memory used to save/store the currently generated reference field potential profile can be released after it has been compared to the measured field potential profile, and then be reused to store the newly generated reference field potential profile. Notably, to decrease the processing time in the RC 16, any analytical modeling computations (in this case, modeling computations involving equation [2]) can be performed during the manufacture of the RC 16 by loading the resulting field potential values within the memory 116 of the RC 16. Although more memory space would be required, the amount of memory space needed would still be substantially reduced by the "shifting" scheme. After all of the field potential profile comparisons have been performed, the stagger of the leads can be quantified, and in particular, the known stagger configuration corresponding to the known reference field potential profile that best matches the measured electrical profile will be selected as the quantified lead stagger.

To determine which of the reference field potential profiles best matches the measured field potential profile, the data can be computationally compared with each other using any one of a variety of comparison functions.

For example, one comparison function that can be used is a correlation coefficient function, such as a Pearson Correlation Coefficient function, which can be expressed as the following equation:

$$r = \frac{\sum_i (MSR_i - M_{MSR})(REF_i - M_{REF})}{sqrt\left(\sum_i (MSR_i - M_{MSR})^2 \sum_i (REF_i - M_{REF})^2\right)},$$

where
r is the coefficient, MSR represents the values of the measured field potential profile (i.e., the first data set), REF represents the values of the current reference field potential profile to be compared (i.e., the second data set), M represents the mean of the data set (either the first data set or the second data set), and i represents a single element of the data set (either the first data set or the second data set). Advantageously, the correlation coefficient is not sensitive to magnitude scaling, and ranges from −1 (perfect inverse correlation) to 1 (perfect correlation). With this function, we seek a maximum—the highest correlation between the actual data and the model-based estimated of the data.

Another comparison function that can be used is a least squares based function, and in particular, a sum of squared differences function, which can be expressed as the following equation:

$$SSD = \sum_i ((MSR_i - REF_i)^2),$$

where
SSD is the sum of squared difference, and MSR, REF, and i have been defined above. The SSD function measures the difference between the actual data and an instance of the model-based estimate of the data. With this function, we seek a minimum—the instance of the model yielding estimates that are the least different from the actual data. Other comparison functions, including cross-correlation functions, wavelet functions, and associated matching measures, may be alternatively used.

Once the stagger between the leads is determined, a graphical representation of the electrodes 26 arranged in accordance with the determined lead stagger can be displayed to the user via display 102 (shown in FIG. 5), which presumably matches the actual stagger of the leads within the patient. If the stagger between the leads 12 indicates that the relative positioning between the leads 12 has moved from an optimal position or is otherwise not in an optimal position, corrective action may be taken, which may fall into two categories—(1) surgical removal or repositioning and (2) reprogramming. Surgical removal or repositioning will typically be employed when it has been determined that one or more of the leads 12 has moved too far to make reprogramming a viable option. If, for example, the therapeutic regimen required that an electrode be located in the baseline location of electrode E9 on second lead 12(2) shown in FIG. 8a, the therapeutic regimen could not be performed once the second lead 12(2) migrated to the location shown in FIG. 8b because there is no longer any electrode in that location.

With respect to reprogramming, information concerning the actual movement (or lack of movement) of each lead 12 will allow reprogramming to proceed in a far more efficient manner than would be the case if the entity tasked with reprogramming (i.e., a physician or the SCS system 10) lacked knowledge that the relative position between lead 12(1) and lead 12(2) has changed due to the movement of one or both leads. Assuming, for example, that the leads 12 illustrated in FIG. 8a were employed in a therapeutic regimen that involved sourcing and sinking stimulation pulses from electrodes E4, E5, and E6 on the first lead 12(1) and electrodes E13 and E14 on the second lead 12(2), after the second lead 12(2) moved to the position illustrated in FIG. 8b, and it was determined that only lead 12(2) moved and that it moved a distance corresponding to two electrodes, the therapeutic regimen may be reprogrammed by simply substituting electrodes E11 and E12, respectively, for electrodes E13 and E14.

Reprogramming may be performed automatically or by a clinician. Automatic reprogramming, which is especially useful when lead migration is being continuously monitored, could be truly automatic (i.e., it would happen without the patient's knowledge). Alternatively, the RC 16 could provide the patient with an indication that at least one lead 12 has moved relative to the other, and provide the patient the option of trying the automatically reprogrammed stimulation regimen or simply reporting the lead migration to the clinician. Reprogramming by the clinician, either in response to a notification from the RC 16 or patient complaint, would typically involve allowing the CP 18 to modify (or simply suggest a modification of) the therapeutic regimen based on the lead migration data from the RC 16. Alternatively, the lead repositioning is recorded for the clinician to review for use during reprogramming, thereby reducing the amount of clinician time (and expense) required to reprogram the therapeutic regimen, as well as the likelihood that an expensive fluoroscopic procedure will be required.

It should be noted that other electrical parameters besides field potential can be used to estimate the cross-lead separation distances. For example, a cross-lead bipolar impedance measurement and a reference intra-lead bipolar impedance measurement can be taken (using an electrode pair as an anode and a cathode and applying a constant current to take an impedance measurement on one of the electrodes). The measured impedance will be proportionate to the field potential drop between the electrode pair. The larger the bipolar impedance is, the larger the distance between the electrode pair. Thus, instead of using field potentials in the "shifting" scheme and "sweeping" strategy described above, impedances can be used to generate measured impedance profiles and reference impedance profiles. Furthermore, although the "shifting" scheme and "sweeping" strategy lend themselves well to their use in a device with limited computational power and memory, such as the RC 16, they can also be utilized in the CP 18. Furthermore, rather than the RC 16 (or the CP 18) performing the above-described relative lead position estimation functions, the IPG 14, itself, can be perform these functions and then send the estimated lead position data to the RC 16 (or CP 18).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

The invention claimed is:
1. A medical system for use with electrode leads, comprising:
memory configured for storing a first reference electrical profile for the electrode leads in a first known staggered configuration, the first reference electrical profile containing a plurality of reference cross-electrode lead electrical parameters; and at least one processor configured for generating instructions to measure a plurality of cross-electrode lead electrical parameters, generating a measured electrical profile of the electrode leads from the measured cross-electrode lead electrical parameters, spatially shifting the first reference electrical profile to generate a second reference electrical profile for the electrode leads in a second known staggered configuration, comparing the measured electrical profile to the first and second reference electrical profiles, and quantifying a longitudinal stagger between the electrode leads based on the comparison.

2. The medical system of claim 1, further comprising:
analog output circuitry configured for being coupled to the electrode leads; and
monitoring circuitry configured for being coupled to the electrode leads;
wherein the at least one processor is configured for generating the measured electrical profile by generating instructions that direct the analog output circuitry to activate at least one electrode carried by one of the electrodes, and that direct the monitoring circuitry to measure an amplitude of the electrical parameter in response to the generated electrical field at each of a plurality of electrodes carried by another of the electrode leads.

3. The medical system of claim 2, wherein the first set of the electrodes comprises an end one of the electrodes carried by the other electrode lead.

4. The medical system of claim 1, wherein the first and second electrode lead stagger configurations are offset from each other by one center-to-center electrode spacing, and the plurality of reference cross-electrode lead electrical parameters is spatially shifted by one center-to-center electrode spacing.

5. The medical system of claim 4,
wherein the memory is further configured for storing a third reference electrical profile for the electrode leads in a third known staggered configuration offset from the first known staggered configuration a distance less than one center-to-center electrode spacing, the third reference profile containing another plurality of reference cross-electrode lead electrical parameters; and
wherein the at least one processor is further configured for spatially shifting the other plurality of reference cross-electrode lead electrical parameters the single electrode spacing to generate a fourth reference electrical profile for the electrode leads in a fourth known staggered configuration that is offset from the third known staggered configuration by one center-to-center electrode spacing, comparing the measured electrical profile to the first, second, third, and fourth reference electrical profiles quantifying the longitudinal stagger between the electrode leads based on the comparison between the measured electrical profile and the first, second, third, and fourth reference electrical profiles.

6. The medical system of claim 1,
wherein the memory is further configured for storing an additional plurality of reference electrical profiles for the electrode leads in an additional plurality of known staggered configurations offset from each other by a distance less than one center-to-center electrode spacing, each of the additional reference electrical profiles containing an additional plurality of reference cross-electrode lead electrical parameters; and
wherein the at least one processor is further configured for comparing the measured electrical profile to the additional reference electrical profiles, and quantifying the longitudinal stagger between the electrode leads based on the comparison between the measured electrical profile and the first, second, and additional reference electrical profiles.

7. The medical system of claim 6, wherein the distance that the additional known staggered configurations are offset from each other is predetermined by the at least one processor.

8. The medical system of claim 6, wherein the at least one processor is configured for dynamically selecting the distance that the additional known staggered configurations are offset from each other based on the comparison between the measured electrical profile and at least some of the additional reference electrical profiles.

9. The medical system of claim 1, wherein the second reference electrical profile is generated subsequent to comparing the measured electrical profile to the first reference electrical profile.

10. The medical system of claim 1, wherein the at least one processor is further configured for estimating the plurality of reference cross-electrode lead electrical parameters by generating an analytical model of the electrode leads.

11. The medical system of claim 10, wherein the analytical model is an optimal fit to a numerical integration model of the electrode leads and tissue.

12. The medical system of claim 1, wherein the at least one processor is configured for selecting the known stagger configuration corresponding to the reference electrical profile that best matches the measured electrical profile as the quantified longitudinal stagger.

13. The medical system of claim 1, wherein the electrical parameter is a field potential of the generated electrical field.

14. The medical system of claim 1, further comprising a display for displaying a graphical representation of the electrode leads with the quantified longitudinal stagger.

15. The medical system of claim 1, further comprising an external control device containing the memory and the at least one processor.

16. The medical system of claim 1, further comprising an implantable medical device comprising a biocompatible casing containing the memory and the at least one processor.

17. The medical system of claim 16, wherein the implantable medical device is an implantable neurostimulation device.

18. The medical system of claim 1, further comprising analog output circuitry configured for delivering electrical stimulation energy to the electrode leads.

* * * * *